United States Patent
Matthys (10) Patent No.: US 9,271,778 B2
(45) Date of Patent: Mar. 1, 2016

(54) METHOD AND AN APPARATUS FOR SCREW REMOVAL

(71) Applicant: RISystem AG, Davos Platz (CH)

(72) Inventor: Romano Matthys, Fideris (CH)

(73) Assignee: RISystem AG, Davos Platz (CH)

( * ) Notice: Subject to any disclaimer, the term of this patent is extended or adjusted under 35 U.S.C. 154(b) by 227 days.

(21) Appl. No.: 14/052,681

(22) Filed: Oct. 11, 2013

(65) Prior Publication Data

US 2015/0105788 A1    Apr. 16, 2015

(51) Int. Cl.
*A61B 17/88* (2006.01)
*A61B 17/56* (2006.01)
*A61B 17/80* (2006.01)
*A61B 17/92* (2006.01)

(52) U.S. Cl.
CPC .................. *A61B 17/88* (2013.01); *A61B 17/56* (2013.01); *A61B 17/808* (2013.01); *A61B 17/8863* (2013.01); *A61B 17/8872* (2013.01); *A61B 17/8894* (2013.01); *A61B 17/92* (2013.01)

(58) Field of Classification Search
CPC ...... A61B 17/56; A61B 17/808; A61B 17/88; A61B 17/8863; A61B 17/8872; A61B 17/8894; A61B 17/92
See application file for complete search history.

(56) References Cited

U.S. PATENT DOCUMENTS 5,382,151 A * 1/1995 Hayes, Jr. ............... B29C 57/04
264/291

* cited by examiner

*Primary Examiner* — Larry E Waggle, Jr.
(74) *Attorney, Agent, or Firm* — Rankin, Hill & Clark LLP (57) ABSTRACT

A method and an apparatus for screw removal from bone plates used in osteosynthesis. The method includes the steps of: performing an incision in the soft tissue surrounding an implanted bone screw having a screw head inserted in an elongated plate hole of a bone plate; positioning an expandable tip of the apparatus in a portion of the plate hole which is not occupied by the bone screw and in the proximity of the screw head of the bone screw, wherein the expandable tip is in an unexpanded position; and widening the plate hole in a lateral direction essentially perpendicular to a major axis of the elongated plate hole by expanding the expandable tip of the apparatus from the unexpanded position to an expanded position.

26 Claims, 6 Drawing Sheets

METHOD AND AN APPARATUS FOR SCREW REMOVAL

BACKGROUND OF THE INVENTION

1. Field of the Invention

The present invention generally relates to surgical methods and an apparatus for explanting bone plates. More particularly, the present invention relates to a method and an apparatus for screw removal from bone plates used in osteosynthesis.

In osteosynthetic treatments of fractured bones so called locking compression plates (LCP) are frequently used. Usually these locking compression plates comprise plate holes for an insertion of bone screws which are configured as combination holes permitting to insert conventional screws or alternatively locking head screws (LHS). These known combination holes are configured as elongated holes having two parts wherein a first part is unthreaded and includes a concave recess and a second part is provided with a conical interior thread. The second part is arranged at one of the two ends of the elongated hole and the interior thread tapers conically towards the underside of the bone plate. Furthermore, the interior thread runs across an arc of more than 180° to firmly receive the conically threaded screw head of the locking head screw. Once implanted the conically threaded screw head of the LHS locks firmly in the correspondingly threaded second part of the combination hole. The concave recess in the first part faces the top side of the plate so as to receive a bone screw having a spherical head thereby allowing the bone screw to be advanced through the plate hole into the bone with an angle relative to the bone plate which is different from 90°.

2. Description of the Related Art

It is known in the art that upon explanting the LCP there is a risk for technical complications which are particularly due to the fact that the LHS could not be loosened because they were jammed in the LCP and/or bonded to the inner surface of the plate hole due to bone/soft tissue ingrowth. If the torque for loosening the locking head screw is too high the screw driver recess in the screw head can become critically damaged or the screw driver tip can break so that the screw driver recess becomes jammed by the broken screw driver tip. In these emergency situations the surgeon usually has special tools available to solve these technical complications. The majority of damaged locking head screws can be removed by using a conical extraction screw driven into the screw driver recess or by drilling off the screw head of the locking head screw. Another procedure currently performed to remove jammed bone screws is to saw the plate apart in the area of the screw hole. However, all of these known procedures are cumbersome and time-consuming.

Thus, there remains a need for an improved method and apparatus for screw removal which allows one to overcome the above disadvantages.

BRIEF SUMMARY OF THE INVENTION

The present invention relates to a method and apparatus for screw removal from bone plates used in osteosynthesis. The method according to the invention comprises the steps of: performing an incision in the soft tissue surrounding an implanted bone screw having a screw head inserted in an elongated plate hole of a bone plate; positioning an expandable tip of an apparatus in a portion of the plate hole which is not occupied by the bone screw and in the proximity of the screw head of the bone screw, wherein the expandable tip is in an unexpanded position; and widening the plate hole in a direction transverse to a major axis of the elongated plate hole by expanding the expandable tip of the apparatus from the unexpanded position to an expanded position.

The advantages of the method according to the invention essentially are that:

by widening the plate hole of the bone plate the exterior thread of the screw head is slightly disengaged from the interior thread of the plate hole so that the torque for loosening the bone screw is reduced;

due to the reduced torque for loosening the bone screw a safe removal of the bone screw from the bone plate is permitted; and a bond between the screw head and the plate hole caused by ingrowth of biological material, e.g. bone tissue and/or soft tissue can be securely separated.

Further advantageous embodiments of the invention can be commented as follows:

In a special embodiment of the method the bone plate is a locking compression bone plate comprising at least one elongated plate hole including a conical threaded part at one end of the plate hole.

In a further embodiment of the method the plate hole is widened laterally by at least 0.5%, preferably by at least 1%, of a diameter of the conical threaded part of the plate hole measured at a lower side of the bone plate.

In another embodiment of the method the plate hole is widened laterally by maximum 4%, preferably by maximum 1.5%, of a diameter of the conical threaded part of the plate hole measured at a lower side of the bone plate.

The plate hole is widened laterally preferably by at least 0.05 mm, more preferably at least 0.07 mm. A slight widening of the plate hole permits to release any jamming between the conical threaded screw head of the locking head screw and the interior conical thread of the plate hole. Preferably, the plate hole is widened laterally by maximum 0.12 mm, preferably maximum 0.10 mm. This configuration permits the advantage that the widening of the plate hole can be performed without having to apply very high forces so that the apparatus can be manually operated.

In another embodiment of the method the expandable tip of the apparatus is positioned in the plate hole with an axis of rotation of a first and a second member of the apparatus extending at an angle of between 5° and 20° with respect to a central axis of a conical threaded part of the elongated plate hole. By this means the advantage can be achieved that the apparatus does not interfere with a screw driver used to remove the bone screw.

In another embodiment the method comprises the additional steps of: inserting a screw driver into a screw driver recess in the screw head of the bone screw; and removing the bone screw from the bone plate.

In again another embodiment of the method the expandable tip of the apparatus includes at least two expandable front edges defining areas of load application.

In a further embodiment of the method the expandable tip is positioned in the elongated plate hole with the front edges of the expandable tip abutting on an inner lateral surface of the elongated plate hole so that the areas of load application are spaced from an end of the plate hole defined by the conical threaded part with a spacing measured in a direction parallel to the major axis of the plate hole of between 70% and 130% of a diameter of the conical threaded part measured at a lower side of the bone plate.

In a further embodiment of the method the elongate plate holes include an unthreaded part adjacent the conical threaded part. Preferably, the expandable tip of the apparatus has a rear end opposite the expandable front edges and the expandable tip is positioned in the elongated plate hole with the rear end of the expandable tip abutting on an end of the elongated plate hole defined by the unthreaded part of the plate hole. Preferably, the bone screw is a locking head bone screw including a conical screw head that is provided with an exterior thread.

In another embodiment of the method the material combination of the bone plate and the bone screw is titanium/titanium, a titanium alloy/titanium, titanium/titanium alloy, a titanium alloy/titanium alloy or stainless steel/stainless steel.

In another aspect of the invention, a method for insertion of bone screws in bone plates is provided which comprises the steps of: positioning an expandable tip of an apparatus in a portion of the plate hole which is not to be occupied by the bone screw and in the proximity of a screw head of a bone screw to be inserted, wherein the expandable tip is in an unexpanded position; widening the plate hole in a direction transverse to a major axis of the elongated plate hole by expanding the expandable tip of the apparatus from the unexpanded position to an expanded position, wherein the bone plate is elastically deformed only; insertion of a bone screw through the plate hole and in a bone without tightening the bone screw; and releasing the apparatus so that the expandable tip of the apparatus returns to its unexpanded position. This procedure permits to avoid jamming of the exterior thread of the screw head and the interior thread of the conical threaded part of the elongated plate hole so that removal of the bone screw can be facilitated.

According to a further aspect of the invention, an apparatus for screw removal from bone plates is provided which comprises: a first and a second member that are coupled rotatably relative to each other about an axis of rotation, wherein each of the first and second members includes a handle and a leg attached thereto, wherein each leg comprises a shaft portion, a rear end and a front end, wherein the front ends of the first and second legs form an expandable tip which in an unexpanded position of the expandable tip is suitable to be inserted into a portion of a plate hole which is not occupied by a bone screw. Upon rotation of the first member relative to the second member by pressing the handles towards each other the expandable tip is expanded from its unexpanded position to its expanded position. The shaft portions of the legs are configured as apart of a circular cylinder with a cylinder axis extending along the axis of rotation, wherein each shaft portion has orthogonal to the axis of rotation a cross-sectional area of a sector of a circle with a central angle of less than 180°. The apparatus further includes a sleeve having a longitudinal axis and coaxially thereto a throughbore, wherein the longitudinal axis coincides with the axis of rotation of the first and second member and wherein the throughbore is configured and dimensioned to receive the shaft portions of the legs and permits a relative rotation thereof about the axis of rotation. The configuration of the shafts permits a contact of their central longitudinal edges at the axis of rotation during rotation of the first and second members so that the two shafts lean against each other so that they do not bend away during expansion of the expandable tip of the apparatus.

In a special embodiment of the apparatus the front ends of the legs each comprise a projection extending in the direction of the axis of rotation, wherein the projections are suitable to be inserted in a first part of an elongated plate hole adjacent a screw head of a bone screw inserted in a second part of an elongated plate hole when the expandable tip is in its unexpanded position.

In a further embodiment of the apparatus each of the projections comprises a peripheral surface having a front section which is directed away from the handle, a rear section which is directed towards the handles, an inner section and an outer section and wherein the rear section has a cutout. The cutout permits the a rotation of the projections relative to each other about the axis of rotation of the first and second members taking account of the arrangement of the axis of rotation at an angle with respect to the bone plate.

In another embodiment of the apparatus the front sections of the peripheral surfaces of the projections form a groove suitable to partly surround a screw head of a bone screw. By this means the projections can be positioned close to the bone screw, so that the elongated plate hole can be widened by having positioned the points of application of forces close to the screw head of the bone screw.

In another embodiment of the apparatus the projections have an overall length measured in the direction from the front sections towards the rear sections permitting the projections to be inserted in a portion of a plate hole which is not occupied by a screw head of a bone screw to be removed. This configuration permits the advantage that the projections cannot slip away from the screw head during expansion of the expandable tip of the apparatus.

In again another embodiment of the apparatus each projection has a front edge formed between the groove and the respective outer section, wherein each front edge extends in the direction of the axis of rotation of the first and second members and is spaced from the axis of rotation by a spacing X.

In a further embodiment of the apparatus the handles are configured as levers wherein the ratio between the length of the levers and the spacing X is about 150:4. By this means the force applied to the lateral walls of the elongated plate hole can be reduced by a factor 37.5 permitting a manual operation of the apparatus.

Preferably, at least the legs of the apparatus have a hardness between 47 HRC (Rockwell hardness) and 60 HRC. A typical value for the hardness is 55 HRC.

In a further embodiment of the apparatus at least the legs of the apparatus are made of high-performance ceramics, preferably of $ZrO_2$.

In another embodiment of the apparatus the legs of the apparatus can be fastenable with respect to each other in the expanded position of the expandable tip.

According to again another aspect of the invention, an assembly is provided which comprises a bone plate comprising at least one elongated plate hole; a bone screw inserted in a conical threaded part of the elongated plate hole; and an apparatus according to the invention. The expandable tip of the apparatus is inserted in a portion of the plate hole which is not occupied by the bone screw and in the proximity of the screw head of the bone screw, wherein the expandable tip is in an unexpanded position.

In a special embodiment of the assembly the elongated plate hole comprises a conical threaded hole with a slot extending along a major axis of the elongated plate hole and wherein a ratio between a width of the slot and a diameter of the conical threaded hole is in a range between 0.7 and 0.85.

In another embodiment of the assembly the elongated plate hole has a length measured along a major axis of the elongated plate hole and wherein a ratio between a diameter of the conical threaded hole and the length of the elongated plate hole is in a range between 0.4 and 0.6, preferably between 0.5 and 0.6.

BRIEF DESCRIPTION OF THE DRAWINGS

Several embodiments of the invention will be described in the following by way of example and with reference to the accompanying drawings in which.

DETAILED DESCRIPTION OF THE INVENTION

FIGS. 1, 2, 5 and 6 illustrate an embodiment of the apparatus 4 for screw removal from bone plates 2 according to the invention, wherein the apparatus 4 includes a first and a second member 12a, 12b that are coupled rotatably relative to each other about an axis of rotation 11. Each of the first and second members 12a, 12b includes a handle 14a, 14b and a leg 15a, 15b attached thereto. Each leg 15a, 15b comprises a shaft portion 17, a rear end 18 and a front end 19, wherein the front ends 19 of the first and second legs 15a, 15b form an expandable tip 5. At least the legs 15a, 15b of the apparatus 4 are made of high-performance ceramics, preferably of $ZrO_2$ and have a hardness between 47 HRC (Rockwell hardness) and 60 HRC and typically of 55 HRC.

Figure 5:
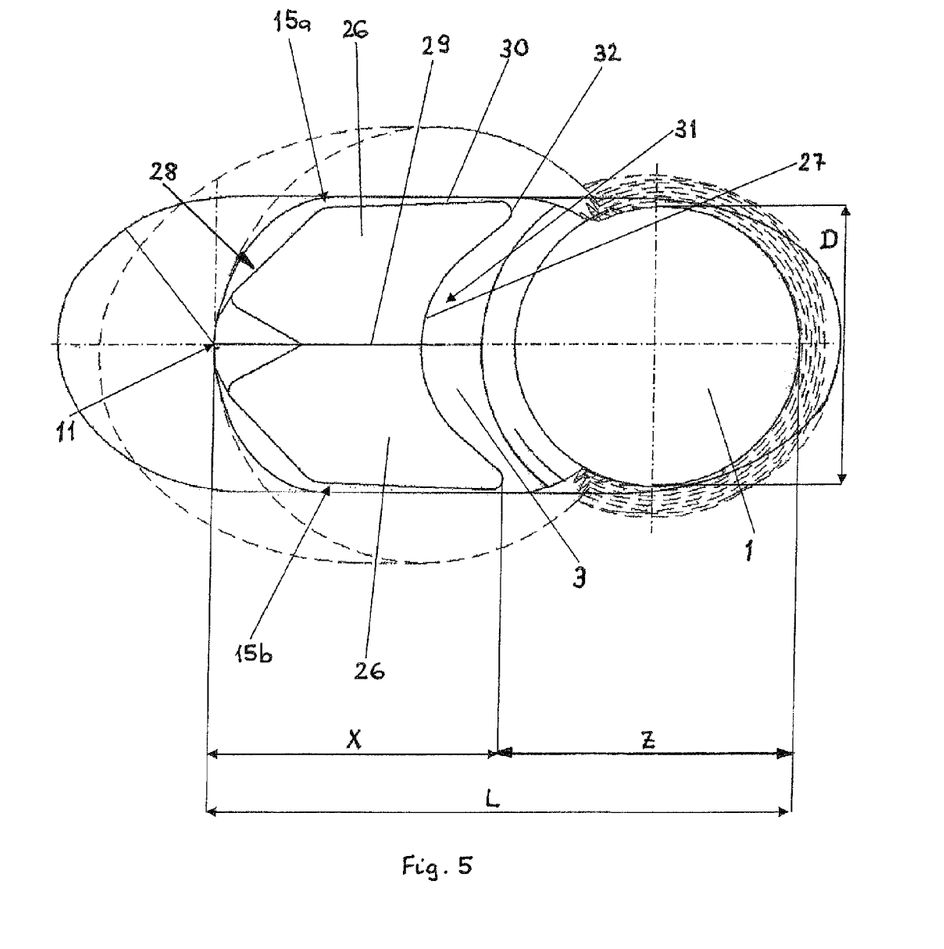
FIG. 5 illustrates a magnified top view on the expandable tip of the apparatus according to the invention illustrated in FIG. 1 when inserted in a combination hole of a bone plate when viewed from the lower side of the bone plate.
Figure 6:
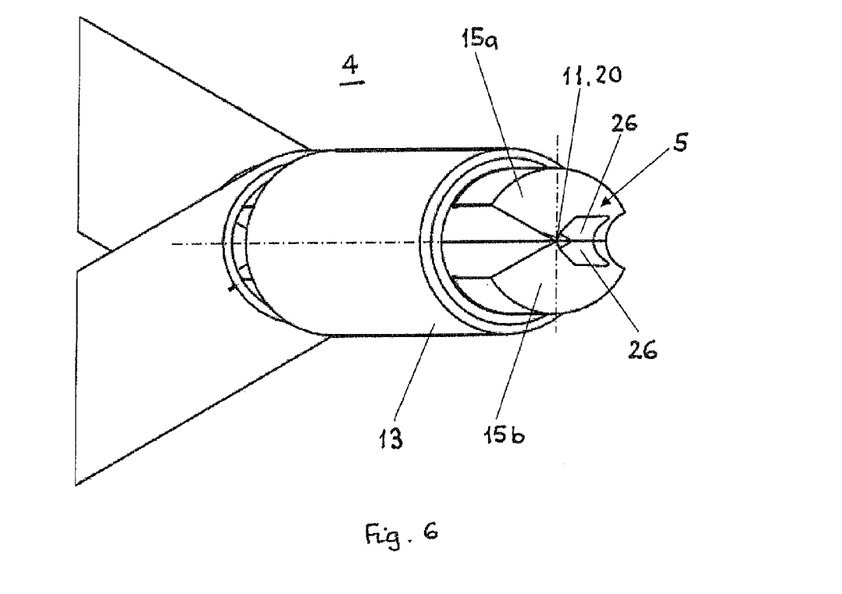
FIG. 6 illustrates a perspective view of the legs of the apparatus according to the invention illustrated in FIG. 1 when viewed from the expandable tip.
Figure 7:
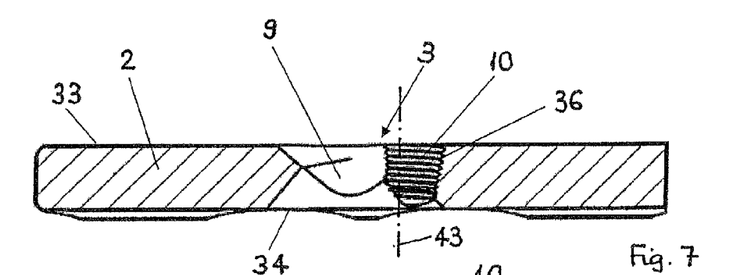
FIG. 7 illustrates a sectional view of a locking compression plate (LCP) with a combination hole.
Figure 8:
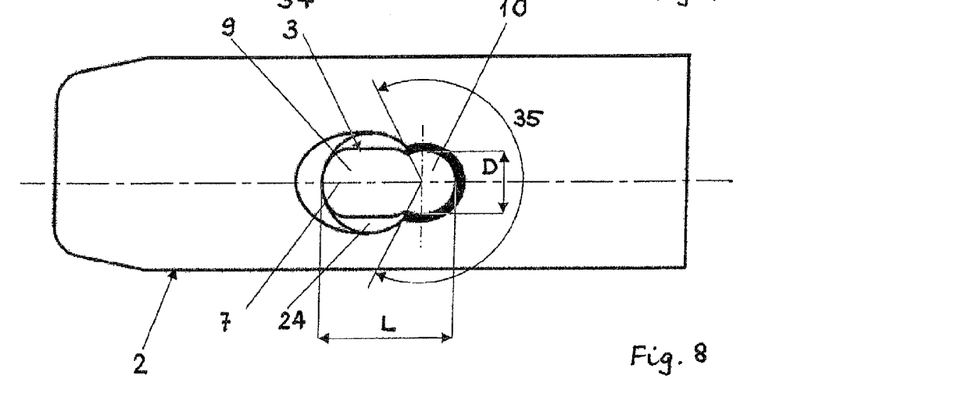
FIG. 8 illustrates a top view of the locking compression plate (LCP) of FIG. 7.

In its unexpanded position the expandable tip 5 is suitable to be inserted into a portion of a plate hole 3 which is not covered by the screw head 6 of a bone screw 1. Upon rotation of the first member 12a relative to the second member 12b by pressing the handles 14a, 14b towards each other the expandable tip 5 is expanded from its unexpanded position to its expanded position. The shaft portions 17 of the legs 15a, 15b are configured as apart of a circular cylinder with a cylinder axis extending along the axis of rotation 11, wherein each shaft portion 17 has orthogonal to the axis of rotation 11 a cross-sectional area of a sector of a circle with a central angle of less than 180°. The apparatus 4 further includes a sleeve 13 having a longitudinal axis 20 and coaxially thereto a through-bore 21. The longitudinal axis 20 of the sleeve 13 coincides with the axis of rotation 11 of the first and second member 12a, 12b and the throughbore 21 is configured and dimensioned to receive the shaft portions 17 of the legs 15a, 15b and permits a relative rotation thereof about the axis of rotation 11. The front ends 19 of the legs 15a, 15b each comprise a projection 26 extending in the direction of the axis of rotation 11, wherein the projections 26 are suitable to be inserted in a first part of an elongated plate hole 3 adjacent a screw head 6 of a bone screw 1 inserted in a second part of an elongated plate hole 3 when the expandable tip 5 is in its unexpanded position. Each of the projections 26 (FIG. 5) comprises a peripheral surface having a front section 27 which is directed away from the handles 14a, 14b, a rear section 28 which directed towards the handles 14a, 14b, an inner section 29 and an outer section 30. The inner sections 29 of the peripheral surface of the projections are at least partly planar and contact each other when the expandable tip 5 of the apparatus 4 is in its unexpanded position so that a middle plane 45 of the apparatus 4 is defined. Upon rotation of the first member 12a relative to the second member 12b the projections 26 rotate about the axis of rotation 11 which extends in the area of the rear ends 37 of the projections 26. Furthermore, the shoulder formed between the projections 26 and the remaining portions of the shafts 17 of the first and second legs 15a, 15b as well as the frontal surfaces of the projections 26 enclose an angle 42 with the axis of rotation 11. The angle 42 preferable amounts to about 75°. The front sections 27 of the peripheral surfaces of the projections 26 form a groove 31 suitable to partly surround a screw head 6 of a bone screw 1 as best seen in FIG. 5. The projections 26 have an overall length measured in the direction from the front sections 27 towards the rear sections 28 permitting the projections 26 to be inserted in a portion of a plate hole 3 which is not covered by a screw head 6 of a bone screw 1 to be removed. Each projection 26 has a front edge 32 formed between the groove 31 and the respective outer section 30. Each front edge 32 extends in the direction of the axis of rotation 11 of the first and second members 12a, 12b and is spaced from the axis of rotation 11 by a spacing X. Exemplarily, the spacing X coincides with the overall length of the projections 26 in the case that the axis of rotation 11 of the first and second members 12a, 12b extends along the rear ends 37 of the projections 26.

Figure 1:
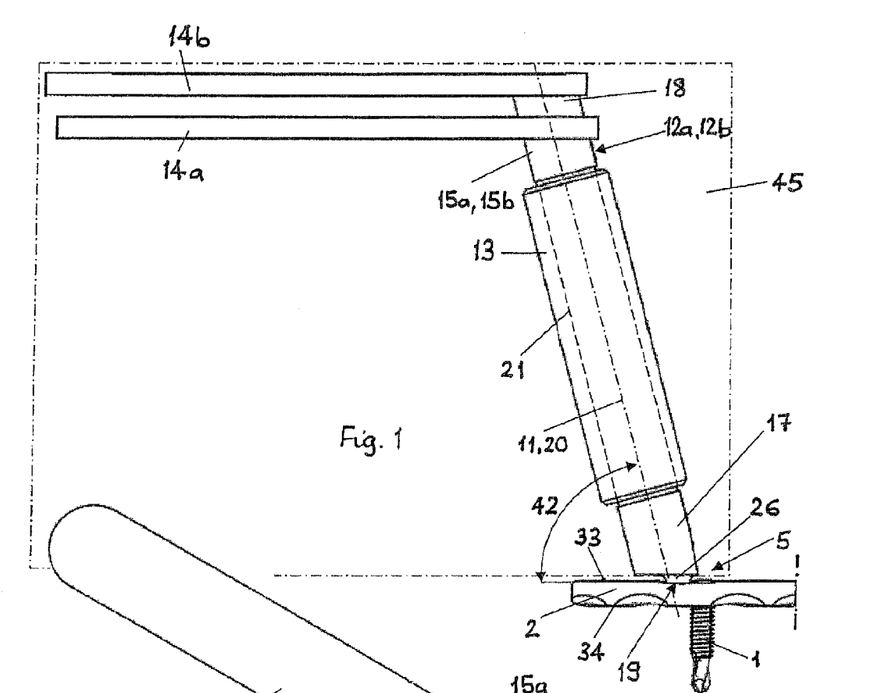
FIG. 1 illustrates a side view of an embodiment of the apparatus according to the invention together with a bone plate and a bone screw.
Figure 2:
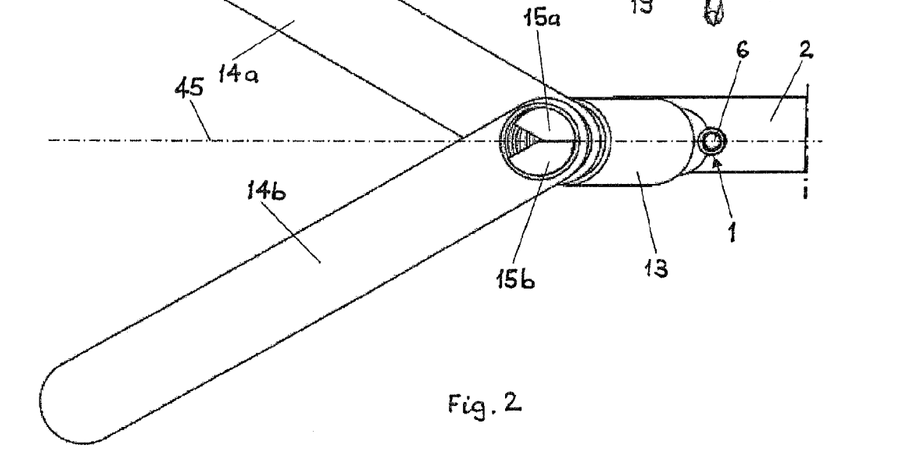
FIG. 2 illustrates a top view of the embodiment of the apparatus according to the invention shown in FIG. 1 together with a bone plate and a bone screw.
Figure 3:
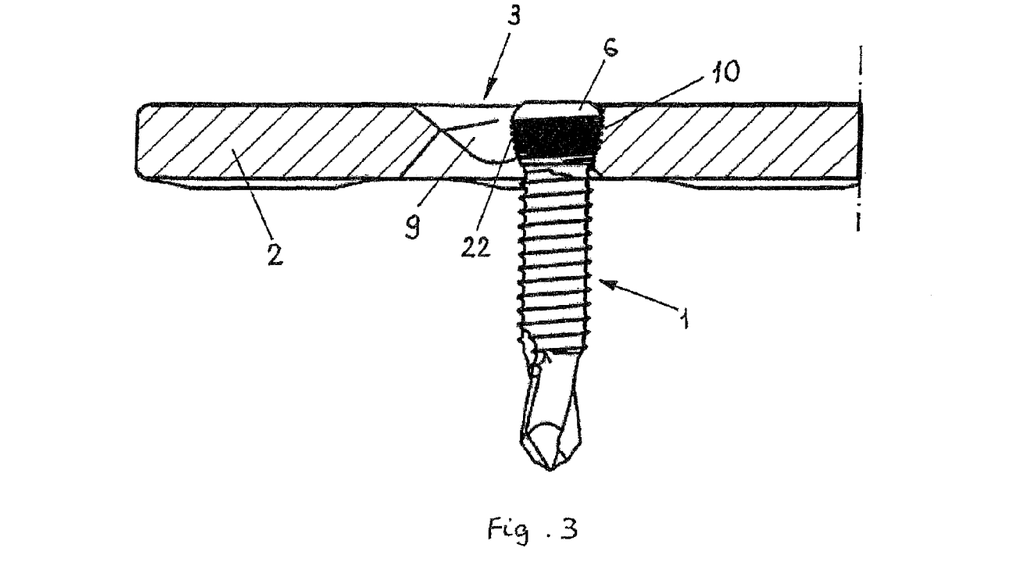
FIG. 3 illustrates a sectional view of a locking compression plate (LCP) with a locking head screw (LHS) inserted in a plate hole.

The handles 14a, 14b are configured as levers and have a length each so that the ratio between the length of the levers and the spacing X is about 150:4. Furthermore, the legs 15a, 15b of the apparatus 4 can be fastenable with respect to each other in the expanded position of the expandable tip 5 by means of e.g. a ratcheting device or a threaded spindle.

Moreover, according to the invention an assembly can be provided including a bone plate 2 comprising at least one elongated plate hole 3, a bone screw 1 inserted in a conical threaded part 10 of the elongated plate hole 3 and an apparatus 4 as described above. Thereby, the expandable tip 5 of the apparatus 4 is inserted in a portion of the plate hole 3 which is not occupied by the bone screw 1 and in the proximity of the screw head 6 of the bone screw 1, wherein the expandable tip 5 is in an unexpanded position.

FIGS. 3, 4, 7 and 8 illustrate a portion of a bone plate 2 configured as a locking compression plate (LCP) and comprising plate holes 3 for an insertion of bone screws 1. The bone plate 2 has an upper side 33 and a lower side 34 facing a bone. The plate holes 3 are configured as combination holes permitting to insert bone screws 1 that are configured either as conventional screws or alternatively as locking head screws (LHS). These combination holes are configured as elongated holes comprising a major axis 7, a first unthreaded part 9 that includes a concave recess 24 extending from the upper side 33 and a second conical threaded part 10. The conical threaded part 10 is arranged at one of the two ends of the elongated plate hole 3 and the interior thread 36 tapers conically towards the lower side 34 of the bone plate 2. The interior thread 36 runs across an arc 35 of more than 180° to firmly receive the conically threaded screw head 6 of the locking head screw.

The interior thread 36 tapers conically toward the lower side 34 of the bone plate 2 and subtends a conical angle of 5-20°, typically of 10°. The length L of the plate hole 3 measured in the direction of the major axis 7 of the elongated plate hole 3 is larger than the diameter D of the conical threaded part 10 of the elongated plate hole 3 measured perpendicularly to the major axis 7 and measured at a lower side 34 of the bone plate 2. The ratio of L/D in the ease of standard LCP bone plates 2 can be within the range of 1.01-3.00 and preferably in the range of 1.5-2.5. Exemplarily, the length L can be about 5.2 mm and the diameter D can be about 2.5 mm.

The position of the conical threaded part 10 of the elongated plate hole 3 at one end of the elongated plate hole 3 allows attaining an enlarged thread zone extending for instance to arc 35 from 190 to 280°, preferably from 200 to 250°. Due to the conical configuration of the conical threaded part 10 the arc 35 of the conical threaded part 10 preferably runs from 180 to 230° when measured at the lower side 34 of the bone plate 2, whereas when measured at the upper side 33 of the bone plate 2 the arc 35 preferably runs from 200 to 270°. The bone screw 1 can be a locking head bone screw (FIGS. 3 and 4) including a conical screw head 6 that is provided with an exterior thread 22. The material combination of the bone plate 2 and the bone screw 1 is preferably titanium/titanium, a titanium alloy/titanium, titanium/titanium alloy, a titanium alloy/titanium alloy or stainless steel/stainless steel.

Table 1 illustrates exemplary dimensions of the plate hole and the apparatus:

| Diameter of bone screw shaft [mm] | Diameter D of conical threaded part of plate hole [mm] | Length L of plate hole [mm] | Overall length of projections 26 [mm] | Spacing X [mm] between front edge 32 and axis of rotation 11 |
|---|---|---|---|---|
| 2.4 | 2.5 | 5.2 | 2.5 | 1.8 |
| 5 | 5.2 | 10.8 | 5.2 | 3.75 |
| 6.6 | 6.85 | 14.3 | 6.85 | 4.95 |

Figure 9:
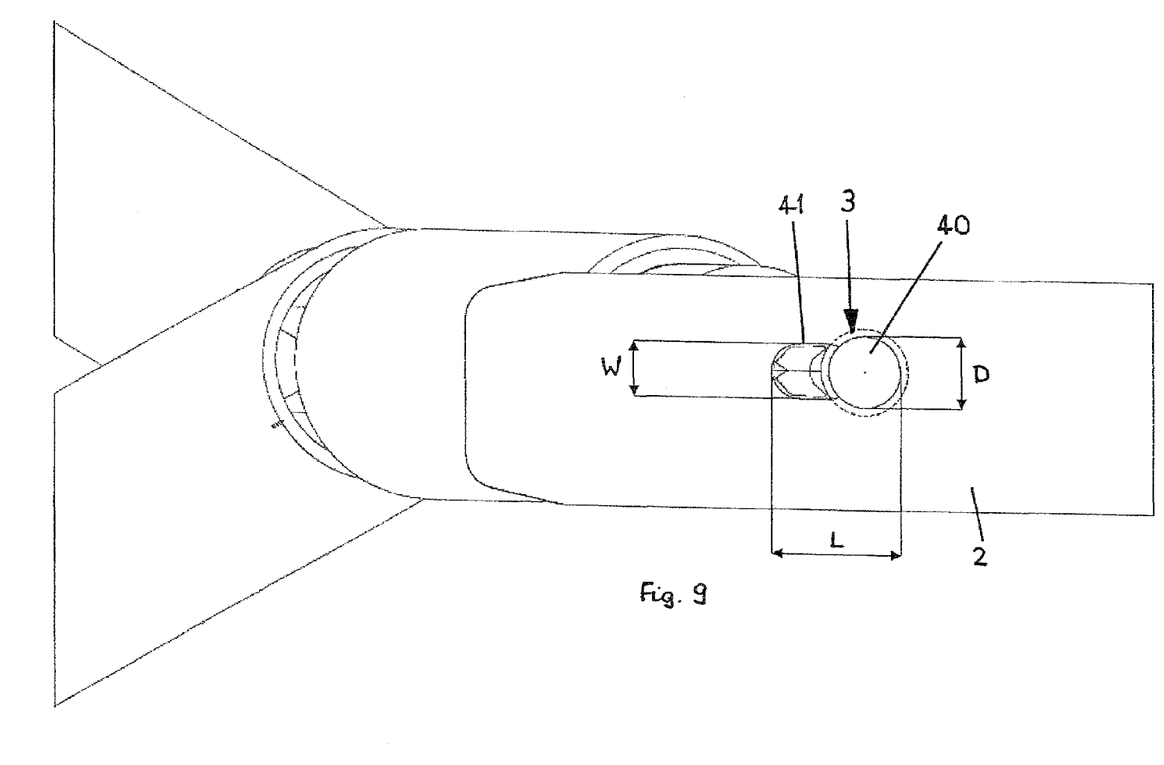
FIG. 9 illustrates a view of the legs of the apparatus according to the invention illustrated in FIG. 1 with a bone plate according to the invention attached thereto when viewed from the lower side of the bone plate.

FIG. 9 illustrates a portion of another embodiment of a bone plate 2 having a plate hole 3 according to one embodiment of the assembly according to the invention. The elongated plate hole 3 of this particular embodiment comprises a conical threaded hole 40 with a slot 41 extending along the major axis 7 of the elongated plate hole 3.

Table 2 illustrates exemplary dimensions of the plate hole and the apparatus:

| Diameter of bone screw shaft [mm] | Diameter D of conical threaded hole [mm] | Length L of plate hole [mm] | Width W of the slot 41 [mm] | Overall length of projections 26 [mm] | Spacing X [mm] between front edge 32 and axis of rotation 11 |
|---|---|---|---|---|---|
| 2 | 2.1 | 3.8 | 1.6 | 1.5 | 1.1 |
| 5 | 5.2 | 9.5 | 4 | 3.75 | 2.7 |
| 7 | 7.3 | 13.3 | 5.6 | 5.25 | 3.8 |

A preferred embodiment of the method for screw removal from bone plates according to the invention can be elucidated in more detail with reference to FIGS. 1-8. An exemplary embodiment of the method comprises the steps of: A) performing an incision in the soft tissue surrounding an implanted bone screw 1 having a screw head 6 inserted in an elongated plate hole 3 of a bone plate 2; B) introducing an apparatus 4 according to the invention into the incision as far as the expandable tip 5 of the apparatus 4 contacts the bone plate 2 in the area of the bone screw 1 to be removed, wherein the expandable tip 5 is in an unexpanded position, and positioning the expandable tip 5 of the apparatus 4 in the portion of the plate hole 3 which is not occupied by the screw head 6 of the bone screw 1 to be removed and in the proximity of the screw head 6 of the bone screw 1; and C) widening the plate hole 3 in a lateral direction essentially perpendicular to a major axis 7 of the elongated plate hole 3 by expanding the expandable tip 5 of the apparatus 4 from the unexpanded position to an expanded position. In a preferred embodiment the method additionally comprises the steps of: 0) inserting a screw driver into a screw driver recess 25 in the screw head 6 of the bone screw 1; and E) removing the bone screw 1 from the bone plate 2.

Figure 4:
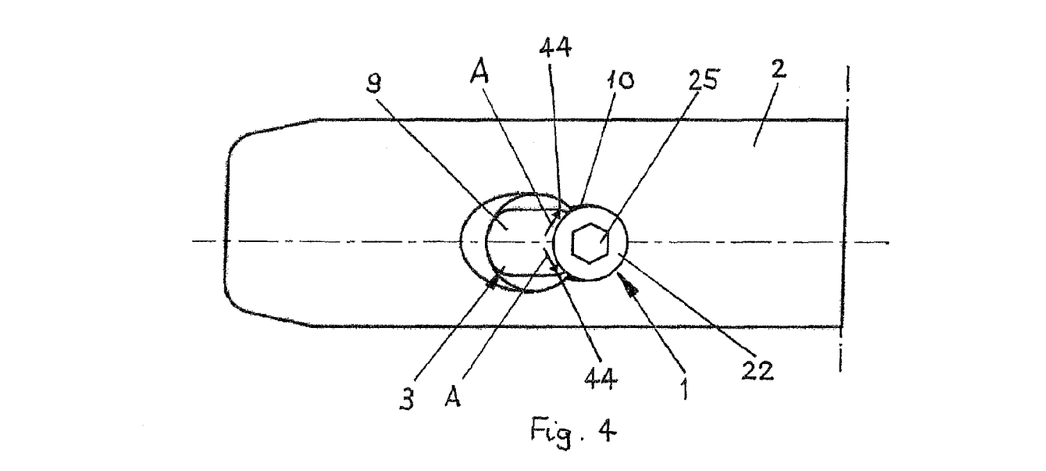
FIG. 4 illustrates a top view on the locking compression plate (LCP) with a locking head screw (LHS) inserted in a plate hole shown in FIG. 3.

The expandable tip 5 of the apparatus 4 includes projections 26 forming two expandable front edges 32 that define areas of load application 44 as indicated by arrows A in FIG. 4. The expandable tip 5 is positioned in the elongated plate hole 3 in the proximity of the screw head 6 of the bone screw 1 with the front edges 32 of the projections 26 abutting on an inner lateral surface of the elongated plate hole 3 so that the areas of load application 44 (FIG. 4) are spaced from the one end of the plate hole 3 which is defined by the conical threaded part 10 (FIG. 3) with a spacing Z measured in a direction parallel to the major axis 7 of the plate hole 3 of about 105% of the diameter D of the conical threaded part 10 measured at a lower side 34 of the bone plate 2 (FIG. 5). By this means the front edges 32 of the projections 26 are in the vicinity of the screw head 6 of the bone screw 1.

Preferably, the expandable tip 5 is positioned in the elongated plate hole 3 with the rear ends 37 of the projections 26 abutting on that end of the elongated plate hole 3 which is defined by the unthreaded part 9 of the plate hole 3. Thereby the expandable tip 5 of the apparatus 4 is positioned in the plate hole 3 with the axis of rotation 11 of the first and second member 12a, 12b extending at an angle of about 15° with respect to the central axis 43 of the conical threaded part 10 of the elongated plate hole 3.

Upon rotation of the first member 12a relative to the second member 12b by pressing the handles 14a, 14b towards each other the expandable tip 5 is expanded from its unexpanded position to its expanded position. During expansion of the expandable tip 5 the plate hole 3 is widened essentially perpendicular to its major axis 7, wherein the plate hole 3 is widened laterally by at least 0.5%, preferably by at least 1% and by maximum 4%, preferably maximum 1.5% of the diameter D of the conical threaded part 10 of the plate hole 3 measured at a lower side 34 of the bone plate 2. Depending on the diameter D of the conical threaded part 10 of the elongated plate hole 3 the widening of the elongated plate hole 3 preferably amounts to at least 0.05 mm, preferably at least 0.07 mm and to maximum 0.12 mm, preferably to maximum 0.10 mm.

An embodiment of the method for insertion of bone screws 1 in bone plates 2 according to the invention comprises the steps of: a) positioning the expandable tip 5 of the apparatus 4 in that portion of the plate hole 3 which is not to be occupied by the bone screw 1 and in the proximity of the screw head 6 of the bone screw 1 to be inserted, wherein the expandable tip 5 is in an unexpanded position; b) widening the plate hole 3 in a lateral direction essentially perpendicular to a major axis 7 of the elongated plate hole 3 by expanding the expandable tip 5 of the apparatus 4 from the unexpanded position to an expanded position, wherein the bone plate 2 is elastically deformed only; c) insertion of a bone screw 1 through the plate hole 3 and in a bone without tightening the bone screw 1; and d) releasing the apparatus 4 so that the expandable tip 5 of the apparatus 4 returns to its unexpanded position. This procedure of inserting the bone screw 1 into the plate hole 3 permits to avoid jamming of the exterior thread 22 of the screw head 6 and the interior thread 36 of the conical threaded part 10 of the elongated plate hole 3.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method for screw removal from bone plates used in osteosynthesis, the method comprising:
   performing an incision in soft tissue surrounding an implanted bone screw having a screw head inserted in an elongated plate hole of a bone plate;
   positioning an expandable tip of an apparatus in a portion of the plate hole which is not occupied by the bone screw and in the proximity of the screw head of the bone screw, wherein the expandable tip is in an unexpanded position; and
   widening the plate hole in a direction transverse to a major axis of the elongated plate hole by expanding the expandable tip of the apparatus from the unexpanded position to an expanded position.

2. The method according to claim 1, wherein the bone plate is a locking compression bone plate comprising at least one elongated plate hole including a conical threaded part at one end of the plate hole.

3. The method according to claim 2, wherein the plate hole is widened laterally by at least 0.5% of a diameter of the conical threaded part of the plate hole measured at a lower side of the bone plate.

4. The method according to claim 2, wherein the plate hole is widened laterally by a maximum of 4% of a diameter of the conical threaded part of the plate hole measured at a lower side of the bone plate.

5. The method according to claim 2, wherein the expandable, tip of the apparatus includes at least two expandable front edges defining areas of load application.

6. The method according to claim 5, wherein the expandable tip is positioned in the elongated plate hole with the front edges of the expandable tip abutting on an inner lateral surface of the elongated plate hole so that the areas of load application are spaced from an end of the plate hole defined by the conical threaded part with a spacing measured in a direction parallel to the major axis of the plate hole of between 70% and 130% of a diameter of the conical threaded part measured at a lower side of the bone plate.

7. The method according to claim 5, wherein the at least one elongate plate hole includes an unthreaded part adjacent the conical threaded part.

8. The method according to claim 7, wherein
   the expandable tip of the apparatus has a rear end opposite the expandable front edges; and wherein
   the expandable tip is positioned in the elongated plate hole with the rear end of the expandable tip abutting on an end of the elongated plate hole defined by the unthreaded part of the plate hole.

9. The method according to claim 1, wherein the expandable tip of the apparatus is positioned in the plate hole with an axis of rotation of a first and second member of the apparatus extending at an angle of between 5° and 20° with respect to a central axis of a conical threaded part of the elongated plate hole.

10. The method according to claim 1, further comprising:
    inserting a screw driver into a screw driver recess in the screw head of the bone screw; and
    removing the bone screw from the bone plate.

11. The method according to claim 1, wherein the bone screw is a locking head bone screw including a conical screw head that is provided with an exterior thread.

12. The method according to claim 1, wherein a material combination of the bone plate and the bone screw is titanium/titanium, a titanium alloy/titanium, titanium/titanium alloy, a titanium alloy/titanium alloy or stainless steel/stainless steel.

13. A method for insertion of bone screws in bone plates comprising:
    positioning an expandable tip of an apparatus in a portion of an elongated plate hole which is not to be occupied by the bone screw and in the proximity of a screw head of a bone screw to be inserted, wherein the expandable tip is in an unexpanded position; and
    widening the plate hole in a direction transverse to a major axis of the elongated plate hole by expanding the expandable tip of the apparatus from the unexpanded position to an expanded position, wherein the bone plate is elastically deformed only;
    inserting a bone screw through the plate hole and in a bone without tightening the bone screw; and
    releasing the apparatus so that the expandable tip of the apparatus returns to its unexpanded position.

14. An apparatus for screw removal from bone plates comprising:
    a first and a second member that are coupled rotatably relative to each other about an axis of rotation, wherein each of the first and second members includes a handle and a leg attached thereto, wherein
    each leg comprises a shaft portion, a rear end and a front end, wherein the front ends of each leg form an expandable tip which in an unexpanded position of the expandable tip is suitable to be inserted into a portion of a plate hole which is not occupied by a bone screw, wherein upon rotation of the first member relative to the second member by pressing the handles towards each other the expandable tip is expanded from its unexpanded position to an expanded position, wherein the shaft portions of the legs are configured as a part of a circular cylinder with a cylinder axis extending along the axis of rotation, wherein each shaft portion has orthogonal to the axis of rotation a cross-sectional area of a sector of a circle with a central angle of less than 180°; and wherein the apparatus further includes a sleeve having a longitudinal axis and coaxially thereto a throughbore, wherein the longitudinal axis coincides with the axis of rotation of the first and second member and wherein the throughbore is configured and dimensioned to receive the shaft portions of the legs and permits a relative rotation thereof about the axis of rotation.

15. The apparatus according to claim 14, wherein the front ends of the legs each comprise a projection extending in the direction of the axis of rotation, wherein the projections are suitable to be inserted in a first part of an elongated plate hole adjacent a screw head of a bone screw inserted in a second part of an elongated plate hole when the expandable tip is in its unexpanded position.

16. The apparatus according to claim 15, wherein each of the projections comprises a peripheral surface having a front section which is directed away from the handle, a rear section which is directed towards the handles, an inner section and an outer section and wherein the rear section has a cutout.

17. The apparatus according to claim 16, wherein the front sections of the peripheral surfaces of the projections form a groove suitable to partly surround a screw head of a bone screw.

18. The apparatus according to claim 17, wherein each projection has a front edge formed between the groove and the respective outer section, wherein each front edge extends in the direction of the axis of rotation of the first and second members and is spaced from the axis of rotation by a spacing (X).

19. The apparatus according to claim 18, wherein the handles are configured as levers and wherein a ratio between a length of the levers and the spacing (X) is about 150:4.

20. The apparatus according to claim 16, wherein the projections have an overall length measured in a direction from the front sections towards the rear sections permitting the projections to be inserted in a portion of a plate hole which is not covered by a screw head of a bone screw to be removed.

21. The apparatus according to claim 14, wherein at least the legs of the apparatus have a hardness between 47 HRC (Rockwell hardness) and 60 HRC.

22. The apparatus according to claim 14, wherein at least the legs of the apparatus are made of high-performance ceramics.

23. The apparatus according to claim 14, wherein the legs of the apparatus are fastenable with respect to each other in the expanded position of the expandable tip.

24. An assembly comprising:

a bone plate comprising at least one elongated plate hole;

a bone screw inserted in a conical threaded part of the elongated plate hole; and an apparatus according to claim 14, wherein the expandable tip of the apparatus is inserted in a portion of the plate hole which is not occupied by the bone screw and in the proximity of a screw head of the bone screw, wherein the expandable tip is in an unexpanded position.

25. The assembly according to claim 24, wherein the elongated plate hole comprises a conical threaded hole with a slot extending along a major axis of the elongated plate hole and wherein a ratio between a width of the slot and a diameter of the conical threaded hole is in a range between 0.7 and 0.85.

26. The assembly according to claim 25, wherein the elongated plate hole has a length measured along a major axis of the elongated plate hole and wherein a ratio between a diameter of the conical threaded hole and the length of the elongated plate hole is in a range between 0.4 and 0.6.

* * * * *